US012746403B2

(12) United States Patent
Liu et al.

(10) Patent No.: US 12,746,403 B2
(45) Date of Patent: Sep. 29, 2026

(54) METHODS AND SYSTEMS FOR OPTIMIZING SHOCK DELIVERY TIME USING AN AUTOMATED EXTERNAL DEFIBRILLATOR

(71) Applicant: Everest Acquisition Entity, LLC, Wilmington, DE (US)

(72) Inventors: Chenguang Liu, Bothell, WA (US); Dawn Blilie Jorgenson, Mercer Island, WA (US); Stacy Earl Gehman, Seattle, WA (US)

(73) Assignee: EVEREST ACQUISITION ENTITY, LLC, Wilmington, DE (US)

( * ) Notice: Subject to any disclaimer, the term of this patent is extended or adjusted under 35 U.S.C. 154(b) by 362 days.

(21) Appl. No.: 18/037,865

(22) PCT Filed: Nov. 17, 2021

(86) PCT No.: PCT/EP2021/081907
§ 371 (c)(1),
(2) Date: May 19, 2023

(87) PCT Pub. No.: WO2022/106435
PCT Pub. Date: May 27, 2022

(65) Prior Publication Data

US 2024/0001130 A1 Jan. 4, 2024

Related U.S. Application Data

(60) Provisional application No. 63/116,955, filed on Nov. 23, 2020.

(51) Int. Cl.
*A61N 1/39* (2006.01)

(52) U.S. Cl.
CPC ....... *A61N 1/39044* (2017.08); *A61N 1/3937* (2013.01)

(58) Field of Classification Search
CPC . A61N 1/39044; A61N 1/3937; A61N 1/3925
See application file for complete search history.

(56) References Cited

U.S. PATENT DOCUMENTS 8,532,766 B2 9/2013 Joo
9,248,306 B2 2/2016 Joo
(Continued)

FOREIGN PATENT DOCUMENTS

JP 2015514500 A 5/2015
WO 2007053820 A1 5/2007

OTHER PUBLICATIONS

International Search Report for PCT/EP2021/081907 filed Nov. 17, 2021.

*Primary Examiner* — Catherine M Voorhees
(74) *Attorney, Agent, or Firm* — Bond, Schoeneck & King, PLLC

(57) ABSTRACT

A method (100) for using an automated external defibrillator (AED) (310), the method comprising: receiving (120), during an active CPR protocol, a signal indicative of motion or lack of motion of the individual; analyzing (130), by the controller, the received signal to determine whether the individual is undergoing motion; providing (140) a direction to begin or continue chest compressions if the controller determines from the received signal that the individual is not undergoing motion; analyzing (150), by the controller, a received ECG signal to determine whether the individual could benefit from a shock delivered from the AED; interrupting (160) the active CPR protocol, if the individual is not undergoing motion and if the individual could benefit from a shock delivered from the AED; and delivering (170) a shock to the individual.

15 Claims, 6 Drawing Sheets

(56) References Cited

U.S. PATENT DOCUMENTS

| | | | | |
|---|---|---|---|---|
| 10,478,630 | B2 | 11/2019 | Gehman | |
| 11,110,288 | B2 | 9/2021 | Kaib | |
| 11,273,314 | B2 | 3/2022 | Gehman | |
| 2011/0224746 | A1 | 9/2011 | Didon | |
| 2012/0245648 | A1 | 9/2012 | Elghazzawi | |
| 2013/0231711 | A1* | 9/2013 | Kaib | G16H 20/30 607/5 |
| 2014/0005738 | A1 | 1/2014 | Jorgenson et al. | |
| 2016/0361227 | A1 | 12/2016 | Freeman et al. | |
| 2017/0361121 | A1* | 12/2017 | Liu | A61N 1/3925 |
| 2018/0161240 | A1 | 6/2018 | Herken | |
| 2018/0169426 | A1 | 6/2018 | Montague et al. | |
| 2019/0105504 | A1* | 4/2019 | Liu | A61B 5/347 |
| 2019/0201281 | A1* | 7/2019 | Freeman | A61B 5/1114 |
| 2020/0085333 | A1* | 3/2020 | Freed | A61B 5/7264 |
| 2020/0139143 | A1 | 5/2020 | Liu | |
| 2021/0387012 | A1 | 12/2021 | Montague | |

* cited by examiner

METHODS AND SYSTEMS FOR OPTIMIZING SHOCK DELIVERY TIME USING AN AUTOMATED EXTERNAL DEFIBRILLATOR

CROSS REFERENCE TO RELATED APPLICATIONS

This application is a national stage application under 35 U.S.C. § 371 of International Application No. PCT/EP2021/081907 filed on Nov. 17, 2021 and published in the English language on May 27, 2022 as International Publication No. WO 2022/106435 A1, which claims priority to U.S. Patent Application No. 63/116,955 filed on Nov. 23, 2020, the entire disclosures of which are incorporated herein by reference.

FIELD OF THE INVENTION

The present disclosure is directed generally to systems and methods for optimizing shock delivery using an automated external defibrillator.

BACKGROUND

Cardiopulmonary resuscitation (CPR) is used to artificially circulate blood, and thus oxygen, through the body of a person who has suffered a cardiac incident until they have a shockable heart rhythm on which a defibrillator can be used, or other medical care can be provided at a hospital or trauma center. The quality of the CPR administered, such as the depth and rate of chest compressions, can vary based on a number of factors such as experience of the rescuer, fatigue, and many other factors.

Automated external defibrillator (AED) devices provide further assistance during a cardiac event. These devices deliver a high-voltage shock to the heart in order to restore normal sinus rhythm in people who are experiencing arrhythmia, such as ventricular fibrillation or ventricular tachycardia. AEDs automatically analyze the electrocardiogram (ECG) rhythm to determine whether defibrillation is warranted and necessary. After deciding that a shock is appropriate and necessary, the AED charges itself to deliver the high-voltage shock, and then instructs the user to press a button causing the device to deliver the defibrillation shock. Many AED devices incorporate sensors which can detect the applied force, depth, and/or rate of chest compressions during CPR.

However, AED devices are mostly passive devices that operate by analyzing a received electrocardiogram (ECG) signal from the individual and issuing commands to direct emergency responders or other users of the device what to do. Commands such as "shock advised, charging," and "clear" inform the user that a shock is impending. After a shock is advised, a fully-automatic AED reminds the user to stay away from the individual and then delivers the shock at the scheduled time. In rare cases, the user doesn't follow the voice prompt to stay away from the individual, and is still in touch with the individual. When the shock is delivered, the electrical current will be conducted to the user and may cause harm.

Additionally, a user may not follow a CPR protocol. In a typical two-minute CPR protocol, the user should perform chest compressions and ventilations. However, a user may stop chest compressions due to distraction, fatigue, or other reasons. If the heart is under ventricular fibrillation (VF) or non-perfusing ventricular tachycardia (VT), and CPR is not being performed, the heart will deteriorate fast and should be defibrillated as soon as possible. If the patient is shockable but CPR is not being performed during a CPR protocol, the chance of survival may be affected. However, current passive AED devices will not preemptively provide a shock due simply to the lack of CPR.

SUMMARY OF THE INVENTION

Accordingly, there is a continued need in the art for AED devices that can either provide or not provide a shock to a user under more conditions, thereby improving the likelihood of survival of the individual experiencing the cardiac event and protecting providers of aid.

The present disclosure is directed to inventive methods and systems for an automated external defibrillator device for use during cardiopulmonary resuscitation. Various embodiments and implementations herein are directed to a system comprising an AED such as a semi-automatic or fully-automatic AED. The AED receives a signal indicative of motion or lack of motion of the individual, and the AED analyzes the signal to determine whether the individual is undergoing motion. If the system determines that there is no motion, the AED provides a direction to begin or continue chest compressions. The AED also receives an ECG signal from the individual and analyzes the signal to determine whether the individual could benefit from a shock delivered from the AED. The system interrupts an active CPR protocol if the individual is not undergoing chest compressions or other motion and if the individual could benefit from a shock delivered from the AED, and delivers the shock to the individual.

Various embodiments and implementations herein are directed to a system comprising an AED such as a fully-automatic AED. The AED receives an ECG signal from the individual and analyzes the signal to determine whether the individual could benefit from a shock delivered from the AED. If the individual could potentially benefit from a shock, the AED schedules a shock. After scheduling the shock, the AED receives a signal indicative of motion or lack of motion of the individual, and the AED analyzes the signal to determine whether the individual is undergoing motion. If the system determines that there is motion, then the AED terminates or delays the scheduled shock.

Generally, in one aspect, a method for using an automated external defibrillator (AED) is provided. The AED comprises (i) a first electrode pad and a second electrode pad, the first and/or second electrode pad configured to obtain at least a portion of an electrocardiogram (ECG) signal from an individual; and (ii) a controller in communication with the first electrode pad and the second electrode pad. The method includes: (i) receiving, during an active CPR protocol, a signal indicative of motion or lack of motion of the individual; (ii) analyzing, by the controller, the received signal to determine whether the individual is undergoing motion; (iii) providing a direction to begin or continue chest compressions if the controller determines from the received signal that the individual is not undergoing motion; (iv) analyzing, by the controller, a received ECG signal to determine whether the individual could benefit from a shock delivered from the AED; (v) interrupting the active CPR protocol, if the individual is not undergoing motion and if the individual could benefit from a shock delivered from the AED; and (vi) delivering, via the first and/or second electrode pad, a shock to the individual.

According to an embodiment, the method further includes analyzing, following a determination that the individual is undergoing motion, the received signal to determine whether the motion or touching is indicative of one or more chest compressions.

According to an embodiment, the method further includes analyzing, after determining that the motion or touching is indicative of one or more chest compressions, the received signal to determine a quality of the one or more chest compressions. According to an embodiment, the quality comprises a rate of chest compressions, a depth of chest compressions, a compression recoil parameter, a compression duty cycle, CPR hand-on time, or a combination thereof.

According to an embodiment, the method further includes providing a direction regarding the determined quality of the one or more chest compressions.

According to an aspect is an AED including a first electrode pad and a second electrode pad, the first and/or second electrode pad configured to obtain at least a portion of an electrocardiogram (ECG) signal from an individual; and a controller in communication with the first electrode pad and the second electrode pad, the controller configured to: (i) receive, during an active CPR protocol, a signal indicative of motion or lack of motion of the individual; (ii) analyze the received signal to determine whether the individual is undergoing motion; (iii) provide a direction to begin or continue chest compressions if the controller determines from the received signal that the individual is not undergoing motion; (iv) analyze, by the controller, a received ECG signal to determine whether the individual could benefit from a shock delivered from the AED; (v) interrupt the active CPR protocol, if the individual is not undergoing motion and if the individual could benefit from a shock delivered from the AED; and (vi) deliver, via the first and/or second electrode pad, a shock to the individual, or request a CPR-free heart rhythm analysis.

According to an aspect is a method for using an AED. The AED comprises (i) a first electrode pad and a second electrode pad, the first and/or second electrode pad configured to obtain at least a portion of an electrocardiogram (ECG) signal from an individual; and (ii) a controller in communication with the first electrode pad and the second electrode pad. The method includes: analyzing, by the controller, a received ECG signal to determine whether the individual could benefit from a shock delivered from the AED; scheduling a shock upon a determination that the individual could benefit from a shock delivered from the AED; receiving, after scheduling the shock but before delivering the shock, a signal indicative of motion or lack of motion of the individual; analyzing, by the controller, the received signal to determine whether the individual is undergoing motion; and terminating or delaying the scheduled shock if the received signal indicates that the individual is undergoing motion.

According to an embodiment, the method further includes announcing, after scheduling the shock, that the shock is impending.

According to an embodiment, the method further includes providing a direction that a shock is impending if the controller determines that the individual is undergoing motion.

According to an embodiment, the method further includes delivering, via the first and/or second electrode pad, a shock to the individual after providing the direction.

According to an aspect is an AED including a first electrode pad and a second electrode pad, the first and/or second electrode pad configured to obtain at least a portion of an electrocardiogram (ECG) signal from an individual; and a controller in communication with the first electrode pad, the second electrode pad, and the sensor, the controller configured to: (i) analyze a received ECG signal to determine whether the individual could benefit from a shock delivered from the AED; (ii) schedule a shock upon a determination that the individual could benefit from a shock delivered from the AED; (iii) receive, after scheduling the shock but before delivering the shock, a signal indicative of motion or lack of motion of the individual; (iv) analyze the received signal to determine whether the individual is undergoing motion; and (v) terminate or delay the scheduled shock if the received signal indicates that the individual is undergoing motion.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of an automated external defibrillator configured to analyze one or more signals before providing a shock to an individual experiencing a cardiac event. More generally, Applicant has recognized that it would be beneficial to provide an automated external defibrillator configured to increase the safety of the user and increase the likelihood of survival of the individual. In view of the foregoing, various embodiments and implementations are directed to an automated external defibrillator device comprising: (i) a first electrode pad and a second electrode pad configured to obtain at least a portion of an electrocardiogram (ECG) signal from an individual; and (ii) a controller in communication with the first electrode pad, the second electrode pad, and the sensor. The AED receives a signal indicative of motion or lack of motion of the individual, and the AED analyzes the signal to determine whether the individual is undergoing motion. If the system determines that there is no motion, the AED provides a direction to begin or continue chest compressions. The AED also receives an ECG signal from the individual and analyzes the signal to determine whether the individual could benefit from a shock delivered from the AED. The system interrupts an active CPR protocol if the individual is not undergoing motion and if the individual could benefit from a shock delivered from the AED, and delivers the shock to the individual, or requests a CPR-free heart rhythm analysis.

According to another embodiment, the AED receives an ECG signal from the individual and analyzes the signal to determine whether the individual could benefit from a shock delivered from the AED. If the individual could potentially benefit from a shock, the AED schedules a shock. After scheduling the shock, the AED receives a signal indicative of motion or lack of motion of the individual, and the AED analyzes the signal to determine whether the individual is undergoing motion. If the system determines that there is motion, then the AED terminates or delays the scheduled shock.

The inventive aspects described or otherwise envisioned herein will save human lives. Inefficient CPR, or lack of CPR leads to thousands of preventable deaths every year, even when AED devices are available. The use of an AED that improves the safety of a user and/or is configured to deliver a shock in the absence of CPR, provides numerous life-saving benefits.

Figure 1:
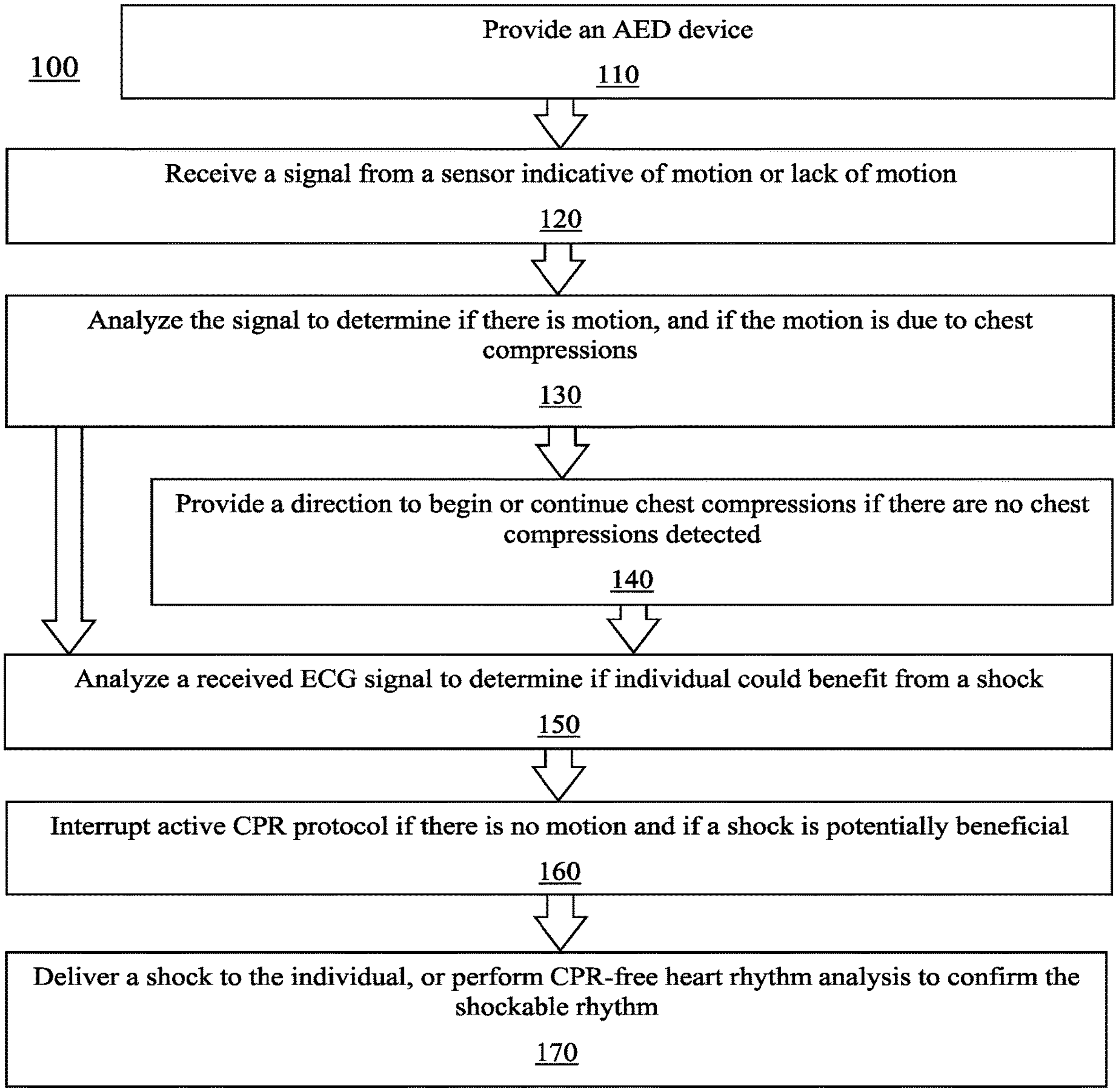
FIG. 1 is a flowchart of a method for using an AED device, in accordance with an embodiment.

Referring to FIG. 1, in accordance with an embodiment, is a flowchart of a method 100 for using an automated external defibrillator (AED). At step 110 of the method, an AED is provided. The AED can be any of the systems described or otherwise envisioned herein. As described or otherwise envisioned herein, the AED can be a permanent installation or can be a portable device. The AED can be a semi-automatic device, a fully automatic device, or any other type of AED.

Figure 3:
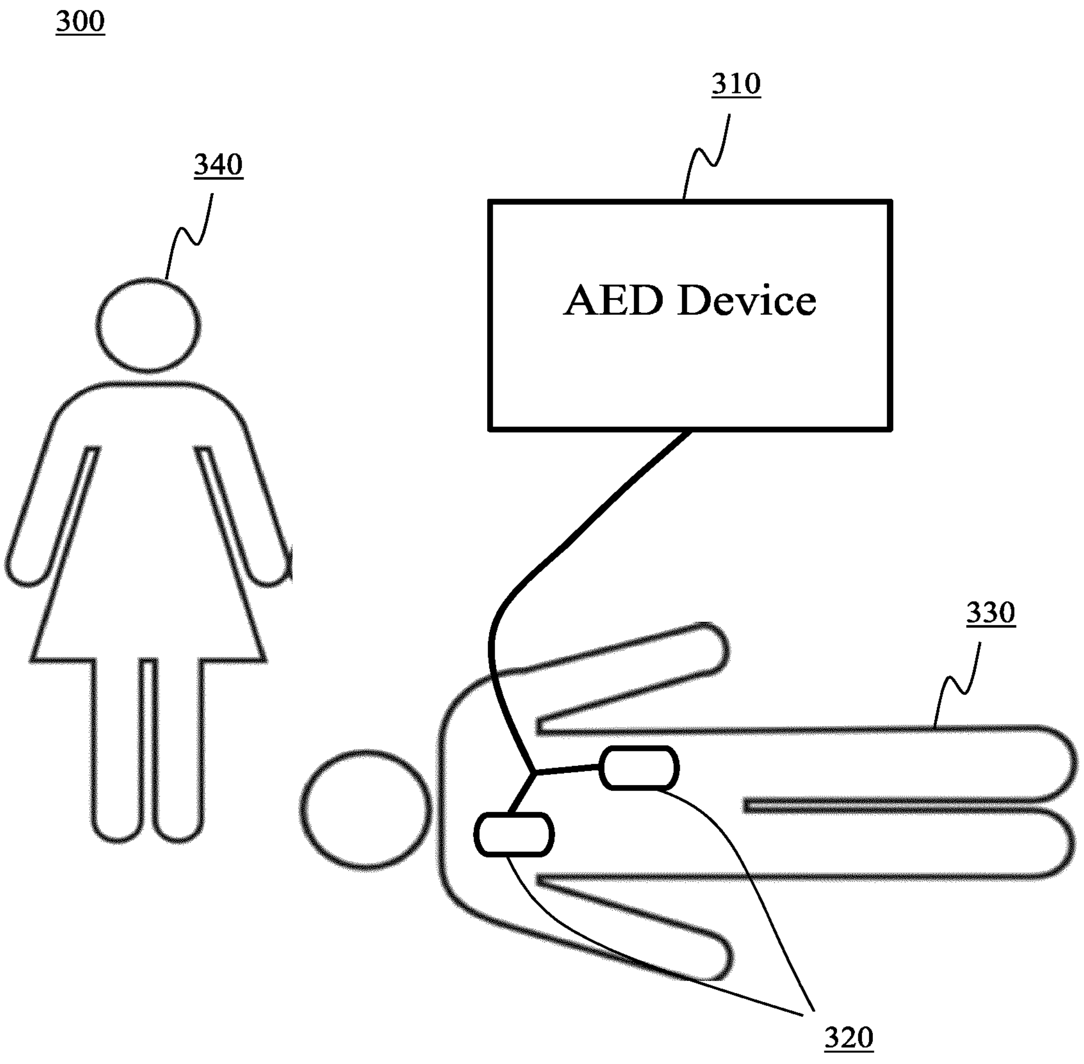
FIG. 3 is a schematic representation of an emergency situation requiring CPR and the use of an AED device, in accordance with an embodiment.

Referring to FIG. 3, in accordance with an embodiment, is a schematic representation of an emergency situation 300 requiring CPR and optionally the use of an AED device 310. Victim 330 is suffering from a cardiac event such as cardiac arrest, and a responder 340 is using the AED device and administering CPR to provide support. The AED device 310 includes first and second electrode pads 320 configured to detect an electrocardiogram (ECG) signal from the victim and further configured to provide, if warranted and necessary, a high-voltage shock to the victim.

Figure 4:
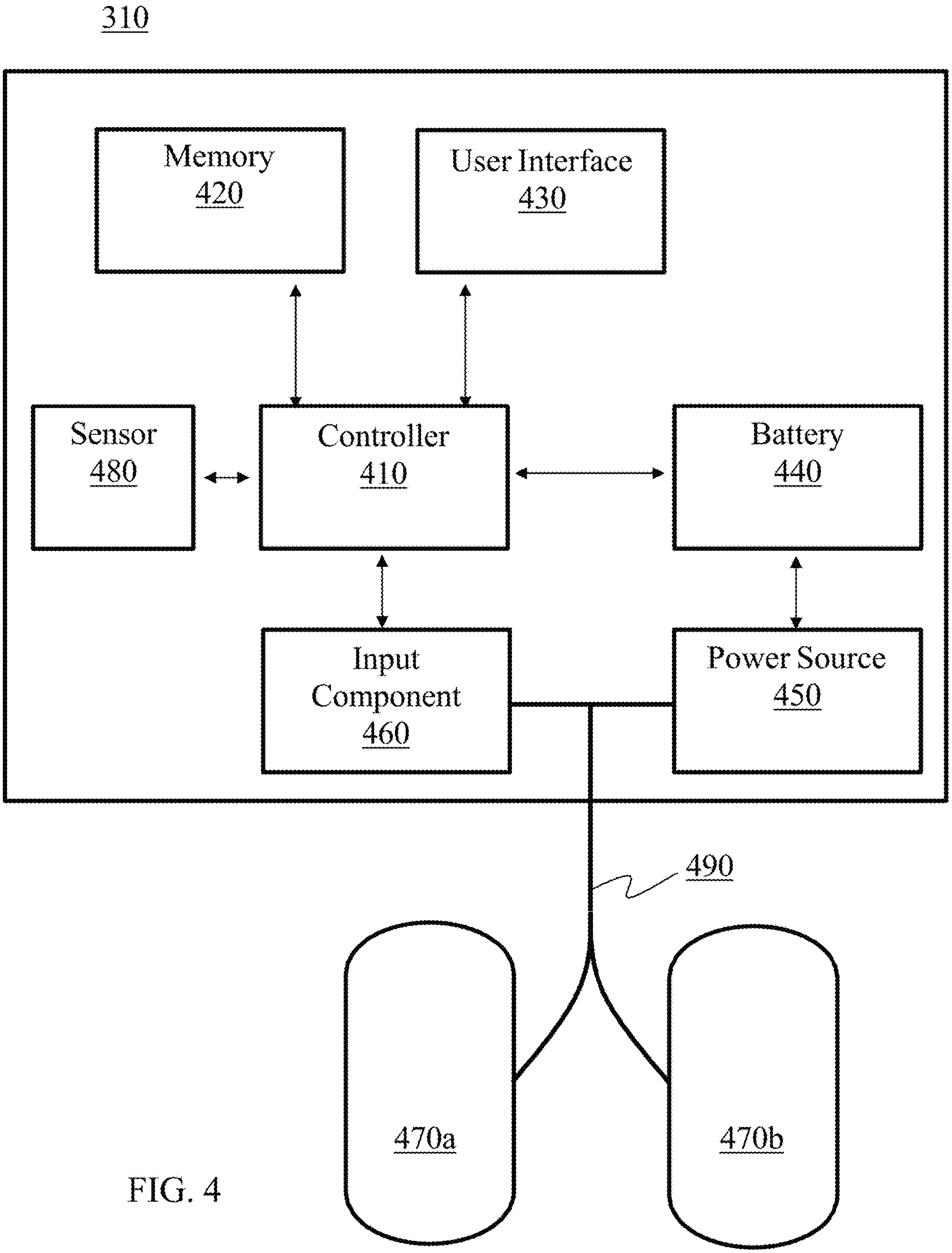
FIG. 4 is a schematic representation of an AED device, in accordance with an embodiment.

Referring to FIG. 4, in accordance with an embodiment, is a schematic representation of an AED device 310. The AED device may be any of the devices or systems described or otherwise envisioned herein. According to embodiment, the AED device comprises one or more of a controller 410, a memory 420, a user interface 430, a battery 440, a power source 450, an input component 460, first and second electrode pads 470*a,b*, and/or sensor 480. The electrode pads are connected by a lead 490 to one or more of the input component and the power source.

According to embodiment, the user interface 430 of the AED device is configured for use in connection with and/or during an emergency situation, as discussed further herein. For example, user interface 430 can comprise a graphical user interface configured to provide instructions to a user during an emergency. User interface 430 may comprise an input/output device, a haptic device, a touch screen, an optical display, a microphone, a keypad, a keyboard, a pointing device, an image capture device, a video camera, an audio output device, or any combination thereof.

The input component 460 may be the controller or a separate component. The input component is configured to receive input from the first and second electrode pads 470*a,b*, such as electrical signals obtained by the pads. For example, the pads can be configured to obtain an electrocardiogram signal from the victim 430 when the pads are placed on the victim's chest. The input component may analyze or process or pre-process the received input, or the input component may pass the received input to the controller or other component of the AED.

The sensor 480, if there is one, may be any sensor configured to or capable of obtaining the sensor data utilized in the methods and systems described or otherwise envisioned herein. According to an embodiment, the sensor is configured to receive an input indicative of motion of the AED and/or electrode pads, which can be interpreted as motion of the individual. Thus, the sensor may be or comprise an accelerometer configured to detect motion. According to an embodiment, the sensor is configured to receive an input indicative of motion or touching of the individual, such as thoracic impedance and/or common mode current (CMC). Impedance and/or CMC, together with ECG, can be used to detect if there is motion of the patient. According to an embodiment, motion can be caused by chest compressions, body movement, agonal breathing, and many other actions. Although the sensor is shown within the body of the AED device, the sensor can optionally be a component of the first electrode pad 470*a* and/or the second electrode pad 470*b*. Alternatively, the sensor can be separate from the AED device, such as an element that is separately stuck to or attached to the individual experiencing the cardiac event. As another option, the sensor can be a component of another device in the vicinity of the individual.

According to an embodiment, motion can be detected by an accelerometer, a force/pressure senor or other sensors. However, motion and compression can still be detected without an extra sensor, since the electrode pads measure three signals: ECG, impedance, and common mode current. ECG, impedance, and common mode current can be used to detect motion and chest compressions by analyzing artifacts caused by motion. Further ECG can be used to detect shockable rhythms. An extra sensor may optionally be utilized as it may provide high accuracy motion detection.

The controller 410 is operatively coupled to memory 420, user interface 430, input component 460, battery 440, power source 450, and/or sensor 480. The controller 410 is capable of executing instructions stored in memory 420 or other data storage or otherwise processing data to, for example, perform one or more steps of the method. Controller 410 may be formed of one or multiple modules. Controller 410 may take any suitable form, including but not limited to a microprocessor, microcontroller, multiple microcontrollers, circuitry, field programmable gate array (FPGA), application-specific integrated circuit (ASIC), a single processor, or plural processors.

Memory 420 can take any suitable form, including a non-volatile memory and/or RAM. The memory 420 may include various memories such as, for example L1, L2, or L3 cache or system memory. As such, the memory 420 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of the device. It will be apparent that, in embodiments where the processor implements one or more of the functions described herein in hardware, the software described as corresponding to such functionality in other embodiments may be omitted.

While device 310 is shown as including one of each described component, the various components may be duplicated in various embodiments. For example, controller 410 may include multiple microprocessors that are configured to independently execute the methods described herein or are configured to perform steps or subroutines of the methods described herein such that the multiple processors cooperate to achieve the functionality described herein. Further, where one or more components of device 310 is implemented in a cloud computing system, the various hardware components may belong to separate physical systems. For example, controller 410 may include a first processor in a first server and a second processor in a second server. Many other variations and configurations are possible.

The battery 440 can comprise any suitable power source or power supply for the AED device. Power source 450, which may be a component of battery 440, is similarly any suitable power source or power supply for the AED device. For example, power source 450 can comprise a high voltage capacitor configured to store energy for defibrillating shocks, where the capacitor is charged by battery 440.

The AED device 310 further comprises a first electrode pad 470*a* and a second electrode pad 470*b*. The electrode pads are operatively coupled to power source 450 via lead 490 and are configured to provide an electrical shock during use of the AED device. According to an embodiment, the first electrode pad 470*a* and the second electrode pad 470*b* are disposable. Thus, after use in an emergency situation, the pads can be disposed of and replaced with new pads. Additionally, the pads may have a predicted lifetime with an expiration date, such that upon expiration the pads can be disposed of and replaced with new pads.

According to an embodiment, the AED device is configured to be activated by a user in an emergency situation, such as when a victim or potential victim is believed to be suffering from a cardia incident. The AED device may be activated by user input, such as by a touch or voice command. In response to being activated, the AED device provides visual and/or audible instructions to the user, including but not limited to instructions regarding placement of the first electrode pad 470*a* and a second electrode pad 470*b* on the victim's chest, administration of CPR, beginning and pausing CPR, warning of an impending shock, administration of a shock, and other instructions.

According to an embodiment, the AED device is configured to receive an input from the first electrode pad 470*a* and/or the second electrode pad 470*b*. For defibrillation purposes, the AED device is configured to receive a signal indicating an electrocardiogram of the victim. The AED device comprises an algorithm configured to receive the signal and analyze the signal to determine if the sinus rhythm of the victim is suitable for administration of a shock via the first electrode pad 470*a* and/or the second electrode pad 470*b*. In some cases, the signal will indicate that a shock would not be beneficial or advantageous. In other cases, the signal will indicate that a shock will be beneficial and/or advantageous. In the latter case, the controller will direct the battery to charge the power source to provide a high-voltage shock to the victim via the first electrode pad 470*a* and/or the second electrode pad 470*b*.

Returning to method 100 in FIG. 1, the AED is engaged in an active CPR protocol that was either automatically triggered by the AED and/or was activated by a user. At step 120 of the method, the system receives a signal from the sensor indicative of motion of, or lack of motion of, the individual. The signal may also or alternatively be indicative of whether the individual is or is not being touched by another person, possibly without motion. The signal may be requested by the controller or may be provided periodically or continually to the controller. The signal may be analyzed immediately, or may be stored for future analysis. As disclosed or otherwise envisioned herein, the sensor may be an accelerometer, an impedance sensor, and/or any other sensor configured to detect motion, thoracic impedance, common mode current, or other inputs indicative of motion or touching.

At step 130 of the method, the controller analyzes the received signal to determine whether the individual is undergoing motion or being touched by another person. The controller can analyze the received signal in real-time or can analyze a stored signal. The analysis may comprise any analysis of the received motion, thoracic impedance, common mode current, or other input indicative of motion or touching. The output of step 130 may be a binary yes/no indication of whether the controller detected motion and/or touching of the individual from the received and analyzed signal. Alternatively, the output may comprise a parameter or other measurement of the detected motion and/or touching of the individual, such as a quality or quantity of the motion or touching. For example, in addition to detection motion, a signal from an accelerometer may comprise an amount of force or movement in addition to the fact of movement.

According to an embodiment, the controller may detect motion and/or touching of the individual from the received signal. Detecting motion and/or touching activates the system to further analyze the received signal to determine whether the motion or touching is indicative of one or more chest compressions. For example, the system may compare the signal analysis to a threshold or known signal analyses comprising chest compressions in order to determine whether the detected motion or touching is indicative of chest compressions.

According to an embodiment, the subsequent analysis by the controller also processes the signal to derive a quality parameter or indicator for the motion. For example, the analysis may comprise processing to determine a rate or pattern of the motion, which can be indicative of the rate of chest compressions. Analysis of the motion may indicate a pattern that indicates a detected motion, potentially compared to a threshold, that can be chest compressions at a certain rate which the controller can calculate. According to current standards from the American Heart Association, for example, users should provide chest compressions at a rate of 100 to 120 compressions/minute to a depth of at least 2 inches (5 cm) for an average depth. Chest compressions above or below this rate may result in ineffective CPR. Accordingly, the controller can compare the calculated rate to the desired rate of 100 to 120 compressions/minute. According to another embodiment, the chest electrode signals are analyzed to separate cardiac-related signals (e.g., electrocardiogram or ECG) to determine motion and/or rate of CPR compressions. According to another embodiment, the quality parameter or indicator for the motion may be compression depth, compression recoil, and/or compression duty cycle. According to another embodiment, the quality parameter or indicator for the motion may be hands-on time, or any other detectable quality parameter or indicator for the motion. For example, if a person does chest compression for four minutes and then rests for one minute, the hands-on time is 80%. A low hands-on time implies low quality CPR.

At step 140 of the method, the AED device provides a direction to a user of the device to begin or continue chest compressions if the controller determines from the received signal that there is no motion or touching, or if the motion or touching is not indicative of one or more chest compressions. For example, the AED device can provide visual and/or audible instructions to the user, including but not limited to instructions regarding placement of the first electrode pad 470*a* and a second electrode pad 470*b* on the victim's chest, administration of CPR, beginning and pausing CPR, warning of an impending shock, administration of a shock, and other instructions.

According to one embodiment, the AED can optionally provide a direction to a user of the device regarding the determined quality of chest compressions. The direction can be provided via the user interface. For example, the direction can be a sound emitted at the desired rate, another audible instruction, a visible instruction, and/or any other instruction to improve or otherwise adjust the analyzed chest compression quality. The system may continue to monitor the received signal(s) to re-analyze the chest compression quality.

At step 150 of the method, the system receives an ECG signal for the individual. According to an embodiment, the first and/or second electrode pad receives the ECG signal which is then transmitted to the input component and to the controller, although other methods of receiving the ECG signal are possible. The ECG signal may be analyzed in real-time, or may be stored for future analysis. The system analyzes the received ECG signal to determine whether the individual could benefit from a shock delivered from the AED. There are many ways to analyze an ECG signal to determine whether a shock is appropriate. There are predetermined heart rhythms that will indicate that a shock would potentially be beneficial, and there are similarly known heart rhythms that indicate that a shock would not be beneficial. Accordingly, the system may compare the ECG and/or an extracted or determined heart rhythm to thresholds or predetermined/preprogrammed heart rhythms or patterns. If there is a match to one of these predetermined/preprogrammed heart rhythms or patterns, which may or may not involve a threshold, the system may determine that a shock is warranted or not warranted. Many other methods and analyses to determine the need or potential benefit of a shock are possible.

At step 160 of the method, the controller has determined that a shock is advisable and has not detected motion and/or touching of the individual. This may indicate that CPR is not being applied, which might be due to inexperience, fatigue, distraction, or other reasons. However, failure to perform CPR can have devastating consequences. A defibrillation shock should be delivered as soon as possible because the heart will become weaker and weaker over time, especially when there is no CPR. Thus, if the patient is shockable and CPR is not being performed, the chance of survival will be negatively affected. Accordingly, the system should apply a shock to the individual even if the timing of shock delivery is abnormal or unexpected. For example, the AED may be running a program that directs the user to perform CPR for a period of time, such as two minutes, between shocks. However, if the system determines during that two-minute CPR window that there is no motion—and therefore likely no CPR—then the system can preempt the program and interrupt the timing in order to optimize survival rates by applying a shock. Therefore, the output of step 160 of the method is a determination that an imminent shock is advisable and the AED will interrupt the active CPR protocol to provide a shock.

According to an embodiment, the controller has determined that a shock is advisable but has detected motion and/or touching of the individual. Accordingly, the system cannot immediately apply a shock as that could cause harm to the user or other person that is moving or touching the individual. Thus the system must provide a direction, such as a warning, that a shock is impending. The system can be designed or programmed to provide a warning a certain time period prior to applying the shock. This may be the time required for charging the system for the delivery of a shock, or any other time period. Accordingly, the system can make an announcement via a user interface. The announcement of the impending shock can be an audible warning clear or otherwise not touch the individual, a visible warning, a haptic warning, and/or any other warning that is intended to capture the attention of the user.

At step 170 of the method, the AED delivers a shock to the individual via the first and/or second electrode pad. This can be accomplished, for example, using known methods and systems for delivering a shock via an AED. The controller can direct the batter 440 to charge the power source 450, and when sufficiently charged the power source can discharge the energy via the lead 490 to the first and/or second electrode pads for delivery to the individual.

After discharge and delivery of the shock to the individual, the AED may be programmed or otherwise designed to return to a monitoring step in the method. For example, the AED may return to step 120 or any other step of the method to begin the process again.

Figure 2:
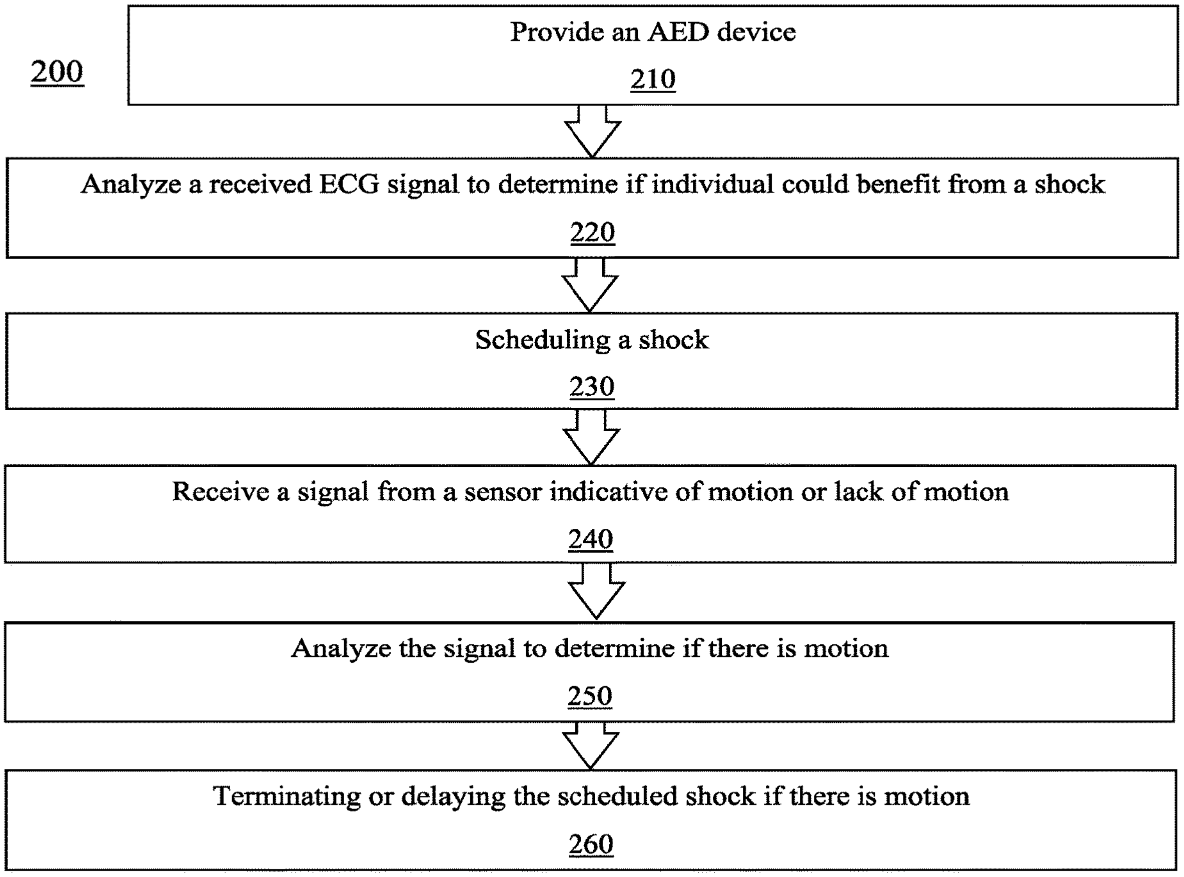
FIG. 2 is a flowchart of a method for using an AED device, in accordance with an embodiment.

Referring to FIG. 2, in accordance with an embodiment, is a flowchart of a method 200 for using an AED. At step 210 of the method, an AED is provided. The AED can be any of the systems described or otherwise envisioned herein. As described or otherwise envisioned herein, the AED can be a permanent installation or can be a portable device. According to an embodiment, the AED is a fully automatic device.

At step 220 of the method, the system receives an ECG signal for the individual. According to an embodiment, the first and/or second electrode pad receives the ECG signal which is then transmitted to the input component and to the controller, although other methods of receiving the ECG signal are possible. The ECG signal may be analyzed in real-time, or may be stored for future analysis. The system analyzes the received ECG signal to determine whether the individual could benefit from a shock delivered from the AED. There are many ways to analyze an ECG signal to determine whether a shock is appropriate. There are predetermined heart rhythms that will indicate that a shock would potentially be beneficial, and there are similarly known heart rhythms that indicate that a shock would not be beneficial. Accordingly, the system may compare the ECG and/or an extracted or determined heart rhythm to thresholds or predetermined/preprogrammed heart rhythms or patterns. If there is a match to one of these predetermined/preprogrammed heart rhythms or patterns, which may or may not involve a threshold, the system may determine that a shock is warranted or not warranted. Many other methods and analyses to determine the need or potential benefit of a shock are possible.

At step 230 of the method, the controller has determined that a shock is advisable and schedules an imminent shock. The timing of the imminent shock can vary depending on the parameters of the device, among other possible variables.

At step 240 of the method, the system receives a signal from the sensor indicative of motion of, or lack of motion of, the individual. The signal may also or alternatively be indicative of whether the individual is or is not being touched by another person, possibly without motion. The signal may be requested by the controller or may be provided periodically or continually to the controller. The signal may be analyzed immediately, or may be stored for future analysis. As disclosed or otherwise envisioned herein, the sensor may be an accelerometer, an impedance sensor, and/or any other sensor configured to detect motion, thoracic impedance, common mode current, or other inputs indicative of motion or touching.

At step 250 of the method, the controller analyzes the received signal to determine whether the individual is undergoing motion or being touched by another person. The controller can analyze the received signal in real-time or can analyze a stored signal. The analysis may comprise any analysis of the received motion, thoracic impedance, common mode current, or other input indicative of motion or touching. The output of step 250 may be a binary yes/no indication of whether the controller detected motion and/or touching of the individual from the received and analyzed signal. Alternatively, the output may comprise a parameter or other measurement of the detected motion and/or touching of the individual, such as a quality or quantity of the motion or touching. For example, in addition to detection motion, a signal from an accelerometer may comprise an amount of force or movement in addition to the fact of movement.

At step 260 of the method, the controller has detected motion or touching, and delays or terminates the imminent shock that was scheduled at step 230 but was not yet delivered. According to one embodiment, the imminent shock is permanently terminated, and the AED can return to a monitoring step in the method. For example, the AED may return to step 220 or any other step of the method to begin the process again. According to another embodiment, the imminent shock is delayed for a certain time period. As an example, the shock is delayed as the AED returns to step 240 of the method to again check for movement. This may continue as long as a shock is still warranted.

Figure 5:
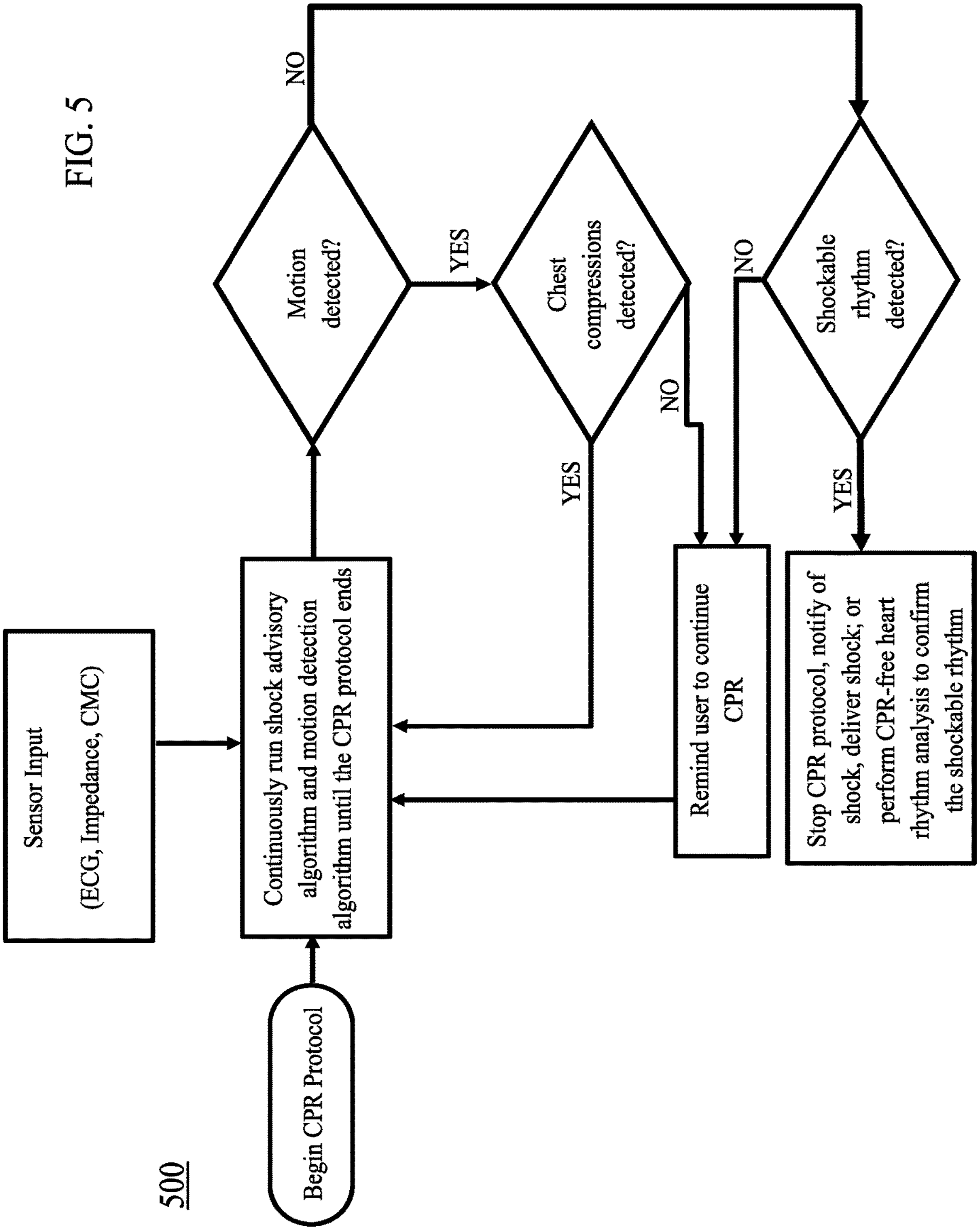
FIG. 5 is a flowchart of a method for using an AED device, in accordance with an embodiment.

Referring to FIG. 5, in one embodiment, is a flowchart showing a method 500 for using an AED device. Once the CPR or resuscitation protocol has started, such as by initiation or activation of the AED device by a user attending to an individual suffering from a cardiac event, the system runs the shock advisory and motion detection methods or algorithms described or otherwise envisioned herein. Accordingly, the AED device is analyzing input data for these analyses, including but not limited ECG input, impedance, CMC, and/or many other types of input.

If motion is detected by the analysis, the system can then perform an additional analysis to determine whether the motion is indicative of chest compressions. If so, the system can return to running the shock advisory and motion detection methods or algorithms, as chest compressions are properly being applied. If chest compressions are not detected but motion is detected, the system can notify the user to begin or continue CPR and then the system can return to running the shock advisory and motion detection methods or algorithms. If neither motion nor shockable heart rhythm is detected, the system can also notify the user to begin or continue CPR and then the system can return to running the shock advisory and motion detection methods or algorithms.

If motion is not detected by the analysis, the system can then ascertain whether a shock would be warranted and/or beneficial for the individual based on the input data and analysis. If a shock is warranted, the system can stop the CPR protocol, notify the user of an impending shock, and can deliver that shock. Alternatively, the system can stop the CPR protocol for a CPR-free heart rhythm analysis to confirm the shockable rhythm. If a shock is delivered, the system can then start a new CPR protocol in which the shock advisory and motion detection methods or algorithms are run.

Figure 6:
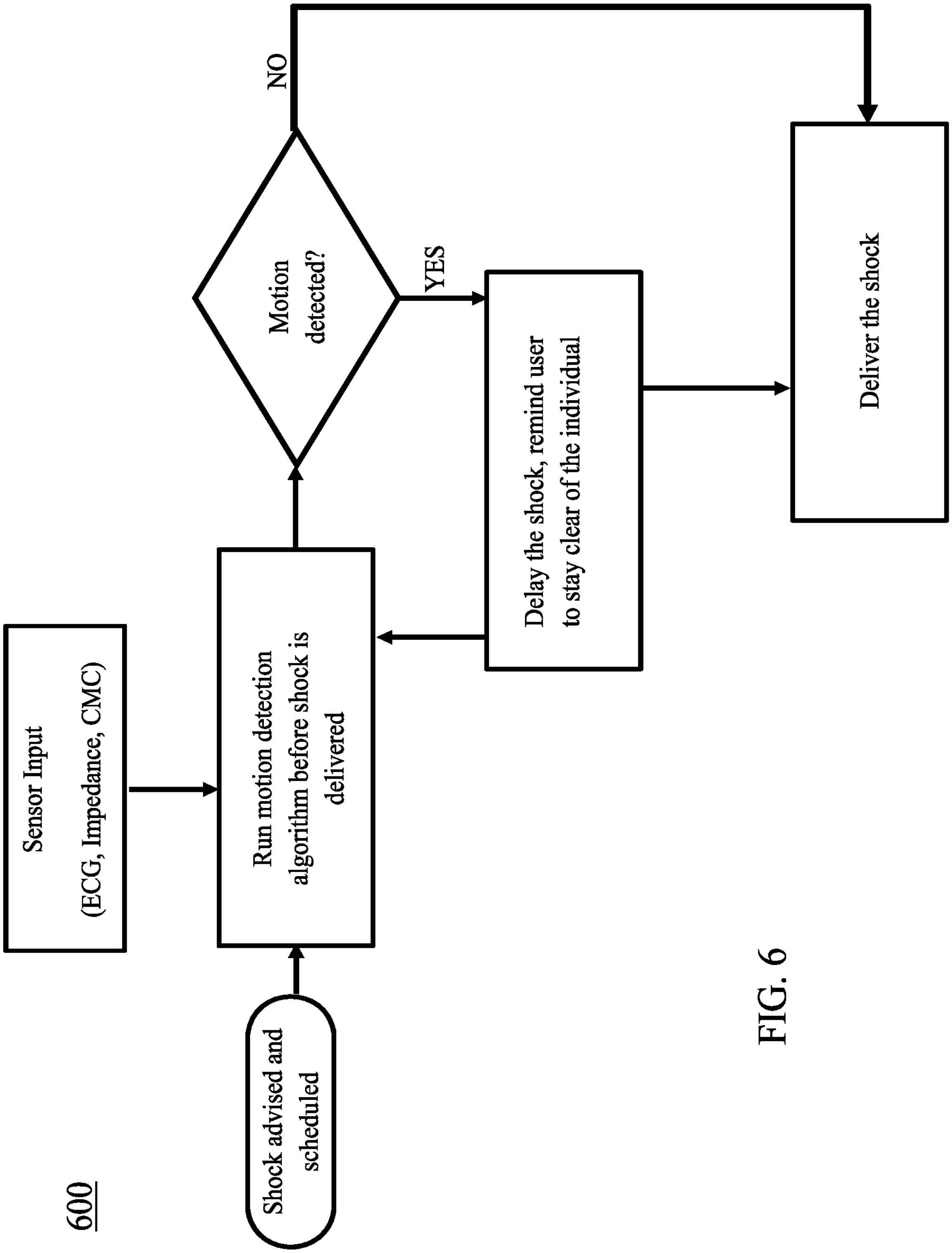
FIG. 6 is a flowchart of a method for using an AED device, in accordance with an embodiment.

Referring to FIG. 6, in one embodiment, is a flowchart showing a method 600 for using an AED device. Once the AED has determined that a shock is advised and has scheduled that shock, the system can again run the motion detection algorithm to determine whether there is no motion of the individual. The AED device is analyzing input data for this analysis, including but not limited ECG input, impedance, CMC, and/or many other types of input.

If motion is not detected, the system can then deliver the shock. If motion is detected, the system can delay the scheduled shock and remind the user to stay clear of the individual. The system can then deliver the shock to the individual. Optionally, after reminding the user, the system may return to a prior step to again check for motion of the individual.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

What is claimed is:

1. A method for using an external defibrillator (AED) comprising: (i) a first electrode pad and a second electrode pad, the first and/or second electrode pad configured to obtain at least a portion of an electrocardiogram (ECG) signal from an individual; and (ii) a controller in communication with the first electrode pad and the second electrode pad, the method comprising:

receiving, during an active CPR protocol, a signal indicative of motion or lack of motion of the individual;

analyzing, by the controller, the received signal to determine whether the individual is undergoing motion;

providing a direction to begin or continue chest compressions when the controller determines from the received signal that the individual is not undergoing motion;

analyzing, by the controller, a received ECG signal to determine whether the individual could benefit from a shock delivered from the AED;

interrupting the active CPR protocol, when the individual is not undergoing motion and when the individual could benefit from a shock delivered from the AED; and delivering, via the first and/or second electrode pad, a shock to the individual.

2. The method of claim 1, further comprising the step of analyzing, following a determination that the individual is undergoing motion, the received signal to determine whether the motion is indicative of one or more chest compressions.

3. The method of claim 2, further comprising the step of analyzing, after determining that the motion is indicative of one or more chest compressions, the received signal to determine a quality of the one or more chest compressions.

4. The method of claim 3, further comprising the step of providing a direction regarding the determined quality of the one or more chest compressions.

5. The method of claim 3, wherein the quality comprises a rate of chest compressions, a depth of chest compressions, a compression recoil parameter, a compression duty cycle, CPR hand-on time, or a combination thereof.

6. An automated external defibrillator (AED), comprising:

a first electrode pad;

a second electrode pad, the first and/or second electrode pad configured to obtain at least a portion of an electrocardiogram (ECG) signal from an individual; and a controller in communication with the first electrode pad and the second electrode pad, the controller configured to: (i) receive, during an active CPR protocol, a signal indicative of motion or lack of motion of the individual; (ii) analyze the received signal to determine whether the individual is undergoing motion; (iii) provide a direction to begin or continue chest compressions when the controller determines from the received signal that the individual is not undergoing motion; (iv) analyze, by the controller, a received ECG signal to determine whether the individual could benefit from a shock delivered from the AED; (v) interrupt the active CPR protocol, when the individual is not undergoing motion and when the individual could benefit from a shock delivered from the AED; and (vi) deliver, via the first and/or second electrode pad, a shock to the individual, or request a CPR-free heart rhythm analysis.

7. The automated external defibrillator (AED) of claim 6, wherein the processor is further configured to analyze, following a determination that the individual is undergoing motion, the received signal to determine whether the motion is indicative of one or more chest compressions.

8. The automated external defibrillator (AED) of claim 7, wherein the processor is further configured to analyze, after determining that the motion is indicative of one or more chest compressions, the received signal to determine a quality of the one or more chest compressions.

9. A method for using an external defibrillator (AED) comprising: (i) a first electrode pad and a second electrode pad, the first and/or second electrode pad configured to obtain at least a portion of an electrocardiogram (ECG) signal from an individual; and (ii) a controller in communication with the first electrode pad and the second electrode pad, the method comprising:

analyzing, by the controller, a received ECG signal to determine whether the individual could benefit from a shock delivered from the AED;

scheduling a shock upon a determination that the individual could benefit from a shock delivered from the AED;

receiving, after scheduling the shock but before delivering the shock, a signal indicative of motion or lack of motion of the individual;

analyzing, by the controller, the received signal to determine whether the individual is undergoing motion indicative of chest compressions; and terminating or delaying the scheduled shock when the received signal indicates that the individual is undergoing motion.

10. The method of claim 9, further comprising the step of announcing, after scheduling the shock, that the shock is impending.

11. The method of claim 9, further comprising the step of providing a direction that a shock is impending when the controller determines that the individual is undergoing motion.

12. The method of claim 11, further comprising the step of delivering, via the first and/or second electrode pad, a shock to the individual after providing the direction.

13. An automated external defibrillator (AED), comprising:

a first electrode pad;

a second electrode pad, the first and/or second electrode pad configured to obtain at least a portion of an electrocardiogram (ECG) signal from an individual; and a controller in communication with the first electrode pad, the second electrode pad, and the sensor, the controller configured to: (i) analyze a received ECG signal to determine whether the individual could benefit from a shock delivered from the AED; (ii) schedule a shock upon a determination that the individual could benefit from a shock delivered from the AED; (iii) receive, after scheduling the shock but before delivering the shock, a signal indicative of motion or lack of motion of the individual; (iv) analyze the received signal to determine whether the individual is undergoing motion; and (v) terminate or delay the scheduled shock when the received signal indicates that the individual is undergoing motion.

14. The automated external defibrillator (AED) of claim 13, wherein the processor is further configured to announce, after scheduling the shock, that the shock is impending.

15. The automated external defibrillator (AED) of claim 13, wherein the processor is further configured to deliver, via the first and/or second electrode pad, a shock to the individual after providing the direction.

* * * * *